United States Patent [19]

Alexander

[11] 4,004,588

[45] Jan. 25, 1977

[54] APPARATUS FOR FLUSHING OVA FROM COWS OR MARES

[75] Inventor: Alan Moana Alexander, Etchingham, England

[73] Assignee: Wrightson NMA Limited, Wellington, New Zealand

[22] Filed: Aug. 25, 1975

[21] Appl. No.: 607,673

[30] Foreign Application Priority Data

May 21, 1975 United Kingdom ............. 21920/75

[52] U.S. Cl. ............................ 128/241; 128/349 B

[51] Int. Cl.² ........................................ A61M 1/00

[58] Field of Search .......... 128/241, 240, 245, 246, 128/349, 350, 344, 348, 304, 276

[56] References Cited

UNITED STATES PATENTS

| | | | |
|---|---|---|---|
| 2,118,631 | 5/1938 | Wappler | 128/349 R |
| 2,211,975 | 8/1940 | Hendrickson | 128/349 R |
| 3,394,705 | 7/1968 | Abramson | 128/349 R |
| 3,929,126 | 12/1975 | Corsaut | 128/349 R |

*Primary Examiner*—John D. Yasko

[57] ABSTRACT

Apparatus for use in flushing ova from cows or mares includes inlet and outlet tubes, which are preferably one within the other, a flexible conduit attached to the end of one of the tubes, an opening in the other tube at that end and a stylet to pass through the one tube and flexible conduit to stiffen the conduit during insertion through the cervix, the stylet being thereafter removable.

11 Claims, 5 Drawing Figures

10
11
11'
12
13
14
15
16
17
18
19
20
21
22
23
24
25
26
27
30
31
32
33
34
35
36
40
41
42

APPARATUS FOR FLUSHING OVA FROM COWS OR MARES

This invention relates to apparatus for flushing ova from cows or mares.

The practice is developing of fertilizing high quality animals, removing the fertilized ova therefrom and replacing them in other animals to complete gestation. The aim is to obtain say three or four offspring per annum from the highest quality animals, rather than the normal one per year as is the case with cows.

Removal of the ova can be performed surgically, by gaining access to the uterus surgically and flushing out the ova. However, it is preferable to perform the task non surgically, and apparatus has already been proposed to penetrate through the cervix to the uterus, and flush the ova therefrom. The present invention relates to apparatus of this type.

As might be expected, this non surgical approach presents problems. For instance, in cows, the cervix is an elaborate organ which is very difficult to penetrate without damage and consequent risk of infection. It has numerous folds which interengage in a tight fashion so that any path therethrough is tortuous unless tissue is substantially displaced. In cows the uterus, which has two "horns", is curved, the path from the tip of each uterine horn, that is the inward end, to the cervix being spiral. In horses also the uterus is curved although it is much shorter. Moreover, the flushing must be performed between days six and fourteen after fertilization when the ova have passed down the fallopian tubes to the tips of the horns. Thus, a flexible part of the flushing apparatus must be presented at the tip, and a flushing system set up entirely within the uterus. The uterus must be blocked with an expansible cuff to ensure that flushing fluid passed in is regained with the ova therein.

According to the present invention, there is provided apparatus for use in flushing ova from mares and cows, such apparatus including an elongate member defining inlet and outlet tubes, an expansible cuff near one end of the member, a flexible conduit attachable to said one end in communication with one of the tubes, an opening to the other tube between the cuff and said end and a stylet which can be passed through the said one tube and the flexible conduit to stiffen the conduit.

The stylet is used to assist penetration of the cervix, through which the flexible tube passes first. After penetration, the stylet can be removed. A path through the cervix having been made, the elongate member can be inserted more easily through the cervix, and this insertion is continued until the free end of the flexible conduit is located at the tip of the uterine horn selected. At this time, the said one end of the elongate member is within the uterus and the expanisble cuff can be expanded to block off the uterus, thus providing a closed system for flushing. A selection of flexible conduits of different lengths is preferably provided in order that with different animals the situation can be obtained that the free end is at the tip of the horn and the expansible cuff at a suitable position in the uterus. Longer flexible conduits are required for cows than for mares, but obviously variations occur within each species. Flushing can then occur. It is preferable for the flexible conduit to be connected to the inlet tube, so that fluid is let in at the tip of the horn and removed through the outlet conduit via an opening just inward of the expansible cuff. Alternatively the reverse process could be used.

It is preferred for the tip of the stilette to be screw threadedly engageable with the inside of the free end of the flexible conduit, where a metal head can be provided, so that the orifice thereof is blocked during insertion through the cervix. The flexible conduit is preferably in the form of a coiled wire, preferably stainless steel, covered with or embedded in a plastics material. It is preferred also for the said opening between the cuff and the said end to be covered during insertion. This may be achieved by providing for the inlet and outlet tubes to be relatively movable longitudinally and for one of them, or preferably, the flexible conduit, to carry a shield to cover the openings, which shield can be moved after insertion to reveal the openings. This precaution helps to keep the openings clean and unblocked, and also allows provision of a large opening which assists in keeping pressure low in the fluid return path. The inlet and outlet tubes are preferably co-axial.

In preferred embodiments, therefore, the two tubes of the elongate member are co-axial, one within the other, the inlet tube being the inner tube and being threadedly attachable to the flexible conduit. The flexible conduit carries a shield which extends around the end of the outer tube and can cover side openings therein, while being movable, with the inner tube, to uncover the openings. The shield can be of gently increasing diameter, thus easing its insertion through the cervix after insertion of the flexible conduit. After insertion, the stylet, which has been within the inner tube and the flexible conduit, is removed, and the inner tube is pushed out of the outer tube a short distance to reveal the openings.

The inner and outer tubes are thus detachable from each other, which is useful for cleaning purposes, and are preferably provided with interengaging means at the end remote from the flexible conduit to keep them in selected relative positions. The outer tube, which is as mentioned, preferably the return tube, can then have a larger operational cross section, thus assisting in the return path pressure low. Preferably, the entire apparatus except the plastics material on the flexible conduit and certain washers and sleeves is of stainless steel so that it can be sterilized in an autoclave.

The expansible cuff can simply comprise an expansible ring fixed around the elongate member. A small air pipe can be provided along the outside of the elongate member to terminate inside the cuff and to be connected at its other end to a one-way valve to which an air pressure source can be attached.

The invention will be more clearly understood from the following description which is given by way of example only with reference to the accompanying drawings in which.

Figures 1, 2, 3, 4, 5:
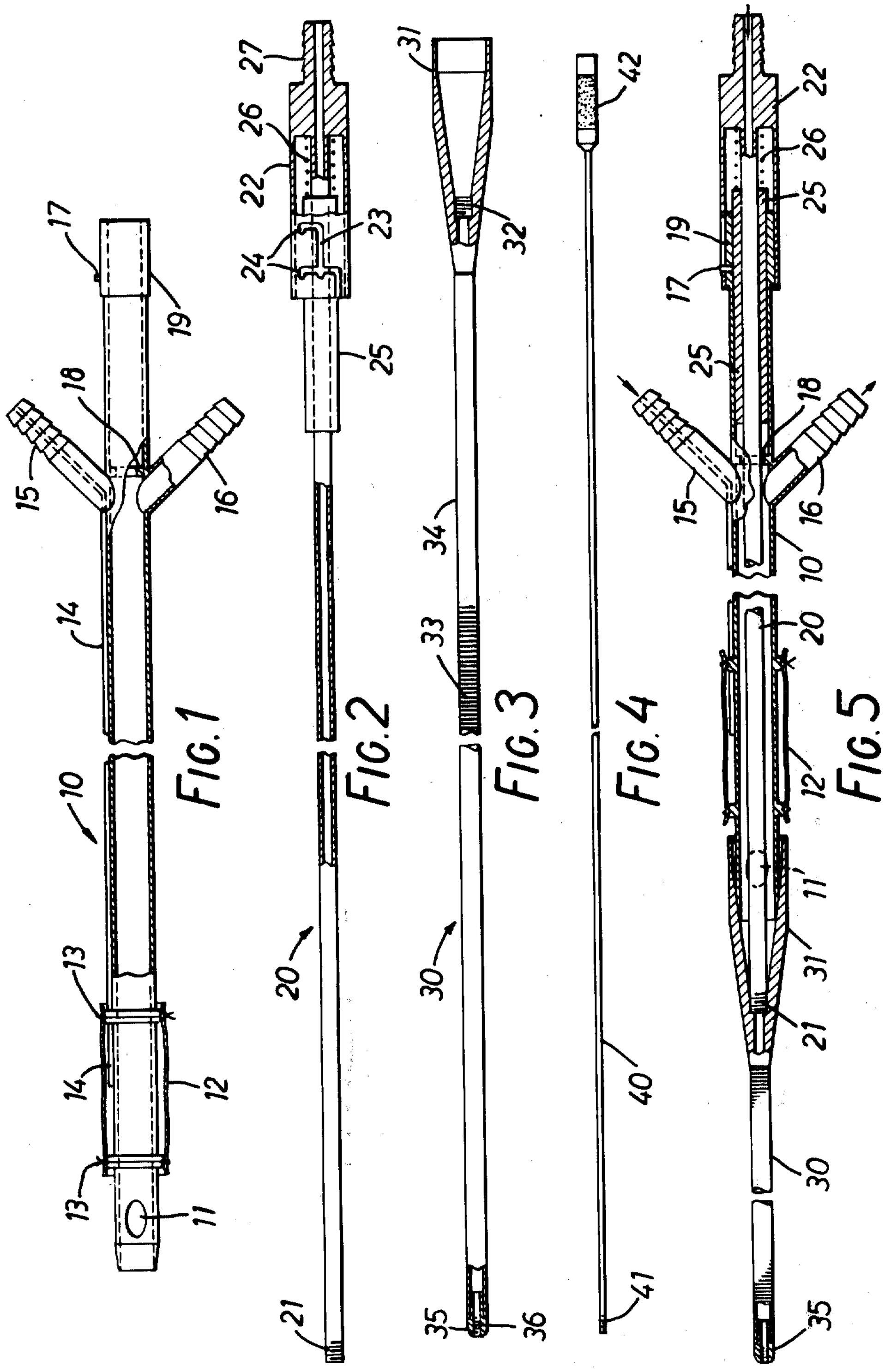
FIG. 1 shows an outer tube of an elongate member of an apparatus of the invention.
FIG. 2 shows an inner tube.
FIG. 3 shows a flexible conduit to be attached to the inner tube.
FIG. 4 shows a stylet to be passed through the inner tube and the flexible conduit attached thereto.
FIG. 5 shows the parts of the preceding Figures assembled, except for the stylet.

In FIG. 1 there is shown an outer tube 10 which is straight and of generally constant diameter. Adjacent one end is shown an opening 11, and another opening may be provided on the opposite side at that end.

Closely inward of the opening is an inflatable cuff 12, shown simply tied to the tube by threads or the like engaging in grooves 13 provided on the outside of the tube for this purpose. A small air tube 14 fixed on the outside of the tube 10 terminates inside the cuff and leads to an air inlet 15 which may include a one-way valve. An outlet 16 is connected to the tube interior opposite the air inlet 15, and in use will collect returned fluid which has passed through the opening 11. At the end of the tube remote from the opening 11 is an enlarged part 19 which will not be passed into the animal, and there is an outwardly projecting pin 17 to engage a slot on the inner tube to be described. Just to the right of the outlet 16 as shown is an abutment 18 inside the tube for a purpose also to be described.

The inner tube 20, shown in FIG. 2, is slightly longer than the outer tube 10. The left end as shown is screw threaded at 21 to engage the flexible conduit of FIG. 3. At its right end, the inner tube 20 supports an enlargement 22 with a cavity of annular cross section to receive the part 19 of the outer tube 10. The enlargement 22 has a slot 23 therein to receive the pin 17 shown in FIG. 1. It can be seen that relative longitudinal movement between the tubes will be allowed when one is within the other, and this movement can be restrained by the pin being engaged in one of two circumferential extensions 24 of the slot. A plastics, preferably nylon, sleeve 25 is slidable on the tube 20 in the region of and partly within the enlargement 22, to extend into the outer tube 10 on assembly. The sleeve 25 is urged by a spring 26 to the left as shown and is adapted to seat on the abutment 18, particularly when the inner tube 20 is pushed to the left during the flushing operation. This seals one end of the space between the tubes which is a part of the fluid return system. The inner tube 20 is the fluid input tube, and a source of fluid, such as a saline solution, can be connected at the end 27 thereof for this purpose.

When the inner tube 20 is located within the outer tube 10, a flexible conduit 30 shown in FIG. 3 can be attached to the left-end of the inner tube as shown. The conduit 30 has a shield 31, internally screw threaded at 32 to engage the tip 21 of the inner tube 20. A washer, typically of nylon, but not shown, will be compressed upon this engagement to make the connection leak proof. The flexible conduit is made of a stainless steel coiled wire 33 covered with synthetic plastics material, such as polytetrafluoethylene, silastic, nylon, or a vinyl material. Part of the coil is shown at 33 but it extends through the length of the flexible conduit. The plastics material, indicated at 34, is preferably of the mentioned type and should preferably be able to withstand sterilization heat treatment in an autoclave.

The shield 31 has a gradually increasing diameter towards the right as shown. Its right end is adapted to cover the opening 11 on assembly of the apparatus in one relative position of the tubes 10 and 12, and to uncover the opening in another position during actual flushing. In this way, the opening cannot get blocked upon insertion. At its left end, as shown, the flexible conduit has a metal tip 35 with a bore 36 therethrough which is partly threaded and has a curved outer end.

Finally, the apparatus includes a stylet shown at 40 at FIG. 4. This is at least as long as the length of the inner tube 20 plus the length of the flexible conduit 30, and is threaded at its tip 41 to engage the threaded bore and the metal tip 35 on the flexible conduit. The stylet also has a handle 42, and is preferably of metal, suitably stainless steel.

FIG. 5 shows the apparatus assembled, except for the stilette. The inner tube 20 is within the outer tube 10, and extends out of both ends thereof. The shield 31 of the flexible conduit is attached to the inner tube, and as shown covers the opening 11. In this condition the stylet can be inserted and engaged with the tip 35. Penetration of the cervix can then be made. A more rigid, alternative stylet can be used if penetration proves to be difficult. After penetration, the stylet is unscrewed and gradually removed as further penetration is made until the opening 11 and the cuff 12 are inside the uterus. Then further insertion is made until the tip 35 of the flexible conduit is at the tip of the uterine horn. The inner tube is then pushed further in, relative to the outer tube, to uncover the opening 11, and to urge the sleeve 25 further into the outer tube to engage against the abutment 18. The cuff 12 is then inflated, and fluid can then be passed in through the inner tube 20, out at the tip of the flexible conduit, and recovered through the opening 11 to be passed through the outer tube and out through the outlet 16 to be collected.

As well as a choice of stylets of different rigidity, there is preferably also provided a choice of flexible conduits of different lengths to suit the animal concerned. The stylet can be in two parts for ease of transport, for instance joined by a flexible non-compressible spring.

Certain dimensions of the apparatus are of some importance in successful operation. In one embodiment, the flexible conduit is of 26 swg stainless steel wire wound to 2 to 3 mm outside diameter. The stainless steel tip of the flexible conduit can then be 3/16th inches (4.75mm) outside diameter. The shield 31 can increase to 6.6 mm diameter over a distance of 39 mm. The flexible conduit can be for instance 5 to 20 inches (130 to 510 mm) long, short distances being used for mares and longer distances for cows. The stylets can be provided for instance of 16 and 18 swg stainless steel wire that is 0.064 inches (1.65 mm) and 0.048 inches (1.22 mm) diameter, and may for instance be 45 inches (1140 mm) long. The inner tube can for instance be 0.104 inches (2.55 mm) outside diameter (12 swg), and about 2 feet (610 mm) long, the outer tube being slightly shorter, for instance by 2 inches (50 mm), and having an outside diameter of 5 millimeters and an inside diameter of 4 millimetres.

I claim:

1. Apparatus for use in flushing ova from mares or cows, such apparatus comprising an elongate member, inlet and outlet tubes defined in said elongate member, an expansible cuff adjacent one end of said member, a flexible conduit, one end of said conduit being removably attached to said one end of said member in communication with one of the tubes, an opening to said other tube between said cuff and said end of said member and a stylet passed through the said one tube and the flexible conduit whereby to stiffen said conduit.

2. Apparatus as claimed in claim 1 wherein the tip of the stylet is screw threadedly engaged with the end of said flexible conduit remote from said one end thereof.

3. Apparatus as claimed in claim 1, wherein the flexible conduit comprises a plastics material strengthened with a coiled wire.

4. Apparatus as claimed in claim 1, wherein the inlet and outlet tubes are relatively movable.

5. Apparatus as claimed in claim 4, and further comprising a movable shield adapted to cover and uncover said opening upon relative movement between said tubes.

6. Apparatus as claimed in claim 5, wherein said shield is supported on said flexible conduit.

7. Apparatus as claimed in claim 5, wherein the shield is tapered in exterior shape and tapers in the direction towards said one end of said member from the other end of said member.

8. Apparatus as claimed in claim 4 and further comprising interengageable means on said tubes whereby said tubes can be maintained in at least two relative positions.

9. Apparatus as claimed in claim 1, wherein said tubes are co-axial, one within the other, so as to comprise inner and outer tubes.

10. Apparatus as claimed in claim 9 and including an abutment inside said outer tube at the end thereof remote from said one end, a sleeve surrounding said inner tube, and means spring urging said sleeve against said abutment to seal the space between said tubes.

11. Apparatus as claimed in claim 1 and further including an air pipe on the exterior of said elongate member, said air pipe having an opening within the expansible cuff.

* * * * *